United States Patent [19]

Batina et al.

[11] Patent Number: 4,700,707

[45] Date of Patent: Oct. 20, 1987

[54] PULSE TO SINE WAVE/SAMPLE DECODER TELEMETRY SYSTEM

[75] Inventors: William P. Batina; Lamar H. Gipson, both of Miami, Fla.

[73] Assignee: Cordis Corporation, Miami, Fla.

[21] Appl. No.: 806,483

[22] Filed: Dec. 9, 1985

[51] Int. Cl.$^4$ .............................................. A61N 1/36
[52] U.S. Cl. ............................. 128/419 PT; 128/903
[58] Field of Search ................. 128/419 PG, 419 PT, 128/903

[56] References Cited

U.S. PATENT DOCUMENTS

| | | | |
|---|---|---|---|
| 3,650,276 | 3/1972 | Burghele et al. | 128/419 G |
| 4,220,156 | 9/1980 | Schulman et al. | 128/903 |
| 4,223,679 | 9/1980 | Schulman et al. | 128/419 PT |
| 4,281,664 | 8/1981 | Duggan | 128/696 |
| 4,361,153 | 11/1982 | Slocum et al. | 128/419 P |
| 4,453,162 | 6/1984 | Money et al. | 128/903 |
| 4,528,987 | 7/1985 | Slocum | 128/903 |
| 4,550,731 | 11/1985 | Batina et al. | 128/419 PT |

Primary Examiner—William E. Kamm

Attorney, Agent, or Firm—George H. Gerstman

[57] ABSTRACT

A telemetry system for communicating with a tank circuit contained in a pacer implanted in a patient includes a telemetry coil and a capacitor connected to the telemetry coil for forming a resonant tank. The telemetry coil is positionable externally on the patient's skin substantially overlying the implanted pacer. The resonant tank has a varying inpedance in response to telemetered data signals from the implanted tank circuit. A clock oscillator generates drive current pulses at a selected frequency to be applied to the resonant tank. A switching transistor generates a pulse waveform having a varying amplitude and frequency in response to the drive current pulses and to the varyng impedance of the resonant tank. A pair of sample and hold circuits are connected in series to function as a clocked filter for sampling the pulse waveform of a varying amplitude and frequency to provide a sample and hold signal. An output circuit is coupled to the sample and hold circuits for recovering of the telemetered data signals in the form of a binary pulse-width modulated signal.

20 Claims, 11 Drawing Figures

PULSE TO SINE WAVE/SAMPLE DECODER TELEMETRY SYSTEM

BACKGROUND OF THE INVENTION

This invention relates generally to telemetry systems for physiological implants and more particularly, it relates to a telemetry system for communicating with an implanted cardiac pacer which samples each drive current pulse applied to a telemetry tank for recovering telemetered data from the pacer.

Heretofore, there have been proposed in the prior art verious telemetry systems for transmitting data into an implanted cardiac pacer as well as systems for signalling out data from the implanted pacer. However, one problem encountered in these prior art systems is that the telemetry reception rate from the pacer could not exceed 4k baud due to the carrier noise in the data recovery circuitry and to the limitation of the bandwidth of the telemetry coil. Another problem experienced in the prior art telemetry systems is that they use a standard active, low pass filter which limited the data recovery rate.

It would therefore be desirable to provide an improved telemetry system for recovering data from an implanted pacer at data rates in excess of 4k baud, but eliminates any carrier noise in the data recovered. The telemetry system of the present invention utilizes a pair of sample and hold circuits connected in series functioning as a clocked filter for sampling of each drive current pulse applied to a telemetry tank. Any change in the electromagnetic field generated by the current pulses as affected by the pacer will be reflectd in changes in the drive current pulses. Thus, by sampling such current pulses telemetered data from the pacer may be recovered from these sampled values.

SUMMARY OF THE INVENTION

Accordingly, it is a general object of the present invention to provide an improved telemetry system for communicating with an implanted cardiac pacer which is relatively simple and economical to manufacture and assemble, but yet overcomes the disadvantages of the prior art telemetry systems.

It is an object of the present invention to provide a telemetry system for receiving data from an implanted pacer at data rates in excess of 4k baud and yet is free of carrier noise in the data recovered.

It is another object of the present invention to provide a telemetry system for communicating with a tank circuit contained in a pacer implanted in a patient which includes a pair of sample and hold circuits connected in series functioning a clocked filter for sampling of each drive current pulse applied to a telemetry tank.

It is still another object of the present invention to provide a system for detecting proximity of an external programming and telemetry unit with respect to an implanted pacer which includes an offset tracking filter responsive to a sample and hold signal to generate a DC signal level representative of the distance of a telemetry coil to the implanted pacer.

In accordance with these and objectives, the present invention is concerned with the provision of a telemetry system for communicating with a tank circuit contained in pacer implanted in a patient which includes a telemetry coil and a capacitor connected to the telemetry coil forming a resonant tank. The telemetry coil is positionable externally on the patient's skin substantially overlying the implanted pacer. The resonant tank has a varying impedance in respone to telemetered data signals from the implanted tank circuit. A clock oscillator generates drive current pulses at a selected frequency which are applied to the resonant tank. A switching device generates a pulse waveform having a varying amplitude and frequency in response to the drive current pulses and to the varying impedance of the resonant tank. A pair of sample and hold circuits connected in series to function as a clocked filter is used to sample the pulse waveform of a varying amplitude and frequency to provide a sample and hold signal. An output circuit is coupled to the sample and hold circuits for recovering of the telemetered data signals in the form of a binary pulse-width modulated signal.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREFERRED EMBODIMENT

Figure 1:
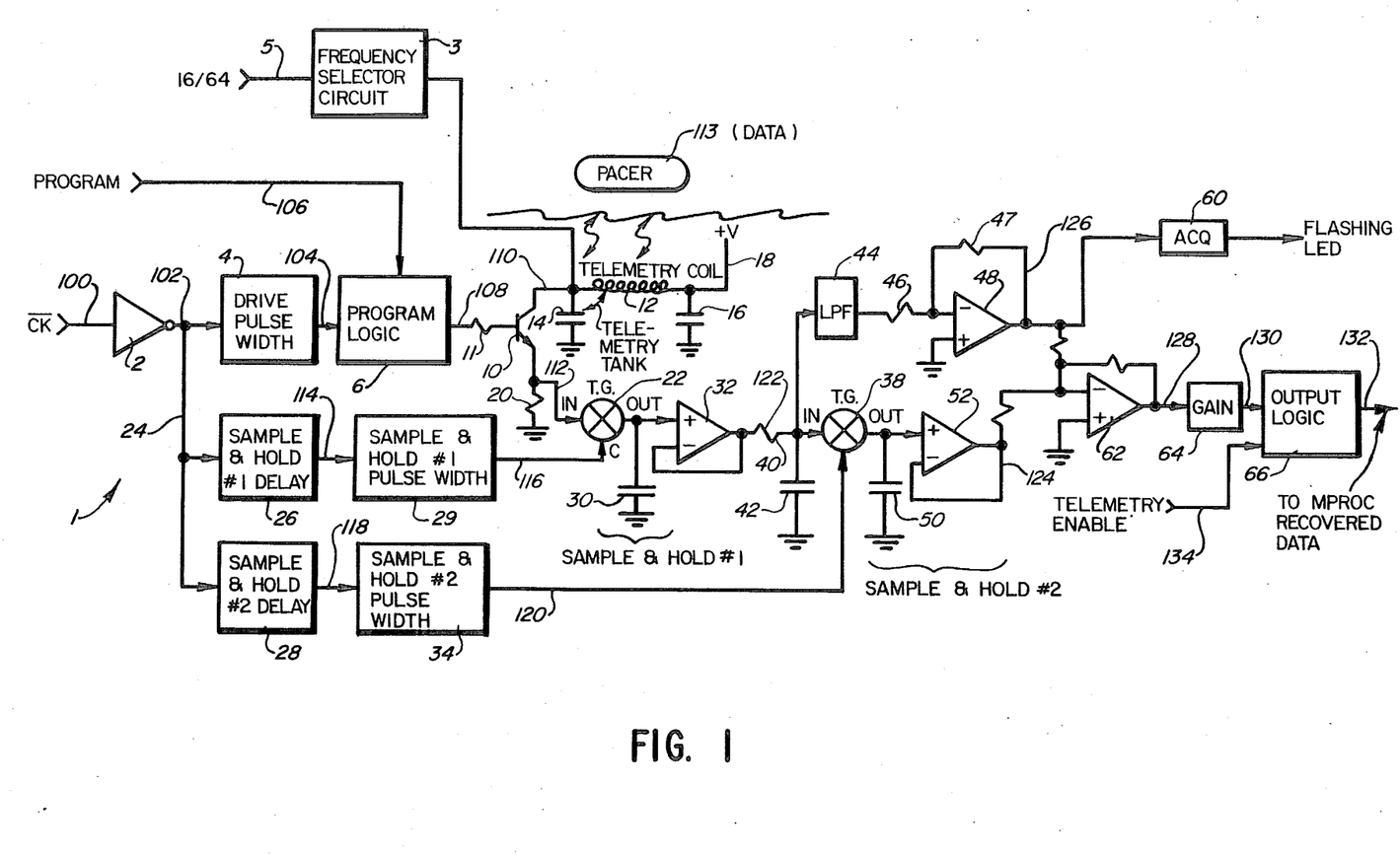
FIG. 1 is a block diagram of a telemetry system for programming an implanted pacer and/or for receiving telemetered data from the pacer, constructed in accordance with the present invention.
Figure 2:
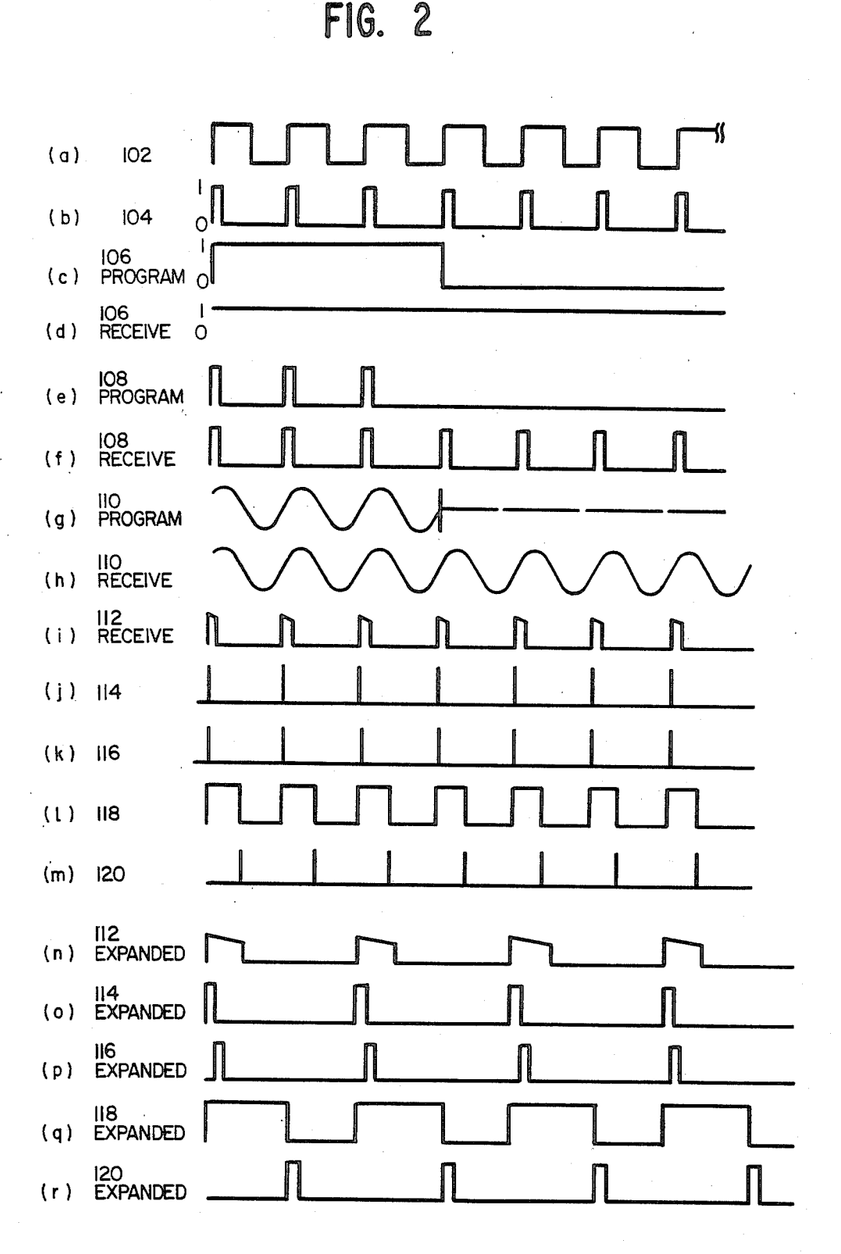
FIG. 2, lines a-r are waveform diagrams useful in understanding the operation of the present invention.

Referring now in detail to the various drawings, there is shown in FIG. 1 in block diagram form a pulse-to-sinewave/sample decoder telemetry system of the present invention which includes an external programming and telemetry unit 1 for programming an implanted pacer 113 and/or receiving telemetered data or message from the pacer. The telemetry unit 1 includes a carrier clock signal on line 100 which is fed to an inverter 2. The clock signal is generated by an oscillator (not shown) which supplies square-wave pulses at 16 kilohertz or 64 kilohertz. The clock signal at the output of the inverter 2 is on line 102 and is shown in FIG. 2, line (a). The inverter output is connected to a monostable (one-shot) multivibrator 4 which is used to adjust or narrow the width of the drive current pulses. The narrowed drive pulses on line 104 are illustrated in FIG. 2, line (b) and are delivered to a program logic switch 6 which is operated to gate the drive current pulses on line 104 through to line 108 depending upon the presence of a program signal on line 106.

During a programming mode when data is being transmitted to the pacer 113, the program signal will be applied to the program logic switch 6 so as to provide a burst of drive pulses on the output line 108. During a telemetry mode when data is being received from the pacer 113, there will be no program signal so that drive current pulses will appear continuously on the output line 108. The input and output signals of the program logic switch 6 during the programming mode are illustrated in FIG. 2, line (c) and (e), respectfully. The input and output signals of the program logic switch 6 during the telemetry mode are depicted in FIG. 2, lines (d) and (f), respectfully. The drive current pulses on the line 108 are connected a switching transistor 10 via a current-limiting resistor 11. The collector of the transistor 10 is connected to one end of a telemetry coil or patient's coil 12 and to one end of a capacitor 14. The telemetry coil 12 and the capacitor 14 form a resonant tank which is tuned to the oscillator frequency for generating an electromagnetic carrier signal. A frequency selector circuit 3 is responsive to a frequency select signal on line 5 for changing the value of the capacitor 14 dependent on whether the oscillator frequency is at 16 kilohertz or 64 kilohertz. The other end of the coil 12 is connected via line 18 to a power supply voltage or potential +V and to one end of a bypass capacitor 16. The other ends of the capacitors 14 and 16 are connected to a ground potential. The collector of the transistor 10 has an output signal on line 110 which is shown in FIG. 2, line (g) during the programming mode. As can be seen, during the programming mode the resonant tank changes the burst of drive current pulses (FIG. 2, line (e)) induced therein into an oscillating field or a sinewave cycle for each drive current pulse. Therefore, a carrier burst can be generated for myriametric programming of the pacer 113.

The collector of the transistor 10 has an output signal on the line 110 which is shown in FIG. 2, line (h) during the telemetry mode. During the telemetry mode, a continuous electromagnetic field of sinewave form is generated from the drive current pulses (FIG. 2, line (f)) induced into the resonant tank. On a cycle to-cycle basis, the electromagnetic energy in the resonant tank will be affected by the varying impedance in a tank circuit (FIG. 4) of the implanted pacer. As the implanted tank circuit is loaded or unloaded, the energy in the telemetry coil 12 and capacitor 14 will change in amplitude and frequency. This combination of amplitude and frequency changes is used to recover data from the pacer.

The emitter of the transistor 10 is connected to the ground potential via a resistor 20 and to an input terminal of a transmission gate 22 via line 112. The clock pulses on the line 102 from the inverter 2 is connected via 24 to a first sample and hold delay circuit 26 which serves to generate output pulses on line 114. The leading edges of the output pulses on the line 114 conicide with the leading edges of the pulses on the line 112. The output pulses on the line 114 is connected to a first sample and hold pulse-width circuit 29 formed of a monostable multivibrator. The output pulses on the line 116 is of an appropriate width which falls within a selected time period of the drive pulses on the line 112. The pulses from the pulse-width circuit 29 serve as control signals which are fed to the control terminal of the transmission gate 22. The output terminal of transmission gate 22 is connected to the non-inverting input of an amplifier 32. The transmission gate 22, amplifier 32 and capacitor 30 define a first sample and hold circuit for sampling and holding (storing) the information in the drive current pulses.

The clock pulses on the line 102 are also connected to a second sample and hold delay circuit 28 which serves to generate output pulses on line 118 whose leading edges also coincide with the leading edges of the driving pulses on the line 112. The output pulses on the line 118 are connected to a second sample and hold pulse-width circuit 34 formed of a monostable multivibrator whose output pulses on line 120 are narrowed and shifted so that the leading edges coincide with the trailing edges of the pulses on the line 118. The various waveforms on the lines 112, 114, 116, 118 and 120 are illustrated in FIG. 2 lines (i) through (m) respectively and the expanded version of these same waveforms are depicted in FIG. 2 lines (n) through (r) respectively.

Figure 3:
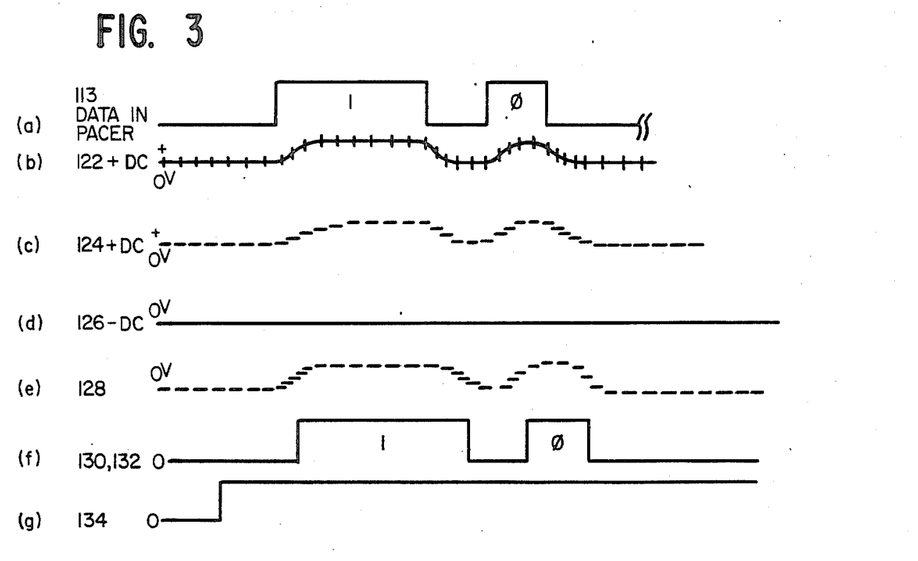
FIG. 3, lines (a)-(g) are another set of waveform diagrams useful in understanding the operation of the present invention.

The output of the amplifier 32 on the line 122 is connected, via a first low pass filter formed of resistor 40 and capacitor 42, to the input terminal of a transmission gate 38 and to a second low pass filter 44. An amplifier 48 with resistors 46, 47 and the second low pass filter 44 define an offset tracking filter. The pulses on the line 120 serve as control signals which are tied to the control terminal of the tranmission gate 38. The transmission gate 38 with capacitor 50 and amplifier 52 define a second sample and hold circuit for transferring the charge from the capacitor 30 to the capacitor 50 so as to eliminate any noise. The first and second sample and hold circuits are connected in series so as to function as a clocked filter. The outputs of the first and second sample and hold circuits on the respective lines 122 and 124 are illustrated in FIG. 3, lines (b) and (c) when modulated telemetered data is being transmitted from the pacer 113 which is shown in FIG. 3, line (a).

The signal at the output of the amplifier 32 on the line 122, which is fed to the offset tracking filter, provides at the output of the amplifier 48 on line 126 a varying DC signal level. This DC signal is inversely proportional to the proximity of the telemetry coil 12 to the implanted pacer 113. An acquisition indicator circuit 60, which receives DC signal, will indicate proximity by increased illumination of a light-emitting diode (LED) or by issuing a sound at an increased pitch. In other words, the light or sound will increased in intensity as there is closer proximity of the telemetry coil 12 to the pacer 113. The DC level on the line 126 is depicted in FIG. 3, line (d).

A summing amplifier 62 is used to sum the DC signal level representive of proximity on the line 126 with the sample and hold or message signal on the line 124. The output of the summing amplifier 62 on the line 128 is shown in FIG. 3, line (e). This sample and hold signal is fed through a gain circuit block 64 which is used to square the same so as to form a binary pulse-width modulated signal on line 130. For example, a one millisecond (ms) pulse is binary "0", a two ms pulse is a binary "1", and the pulse-to-pulse period is three ms. This modulated signal is fed to an output logic circuit 66 which is enabled by a telemetry enabled signal on line 134. The modulated signal on the line 130, which is also the recovered data signal on the line 132 when there is an enable signal, is shown in FIG. 3, line (f). The telemetry enabled signal is shown in FIG. 3, line (g). The recovered data signal on the line 132 is fed through a microprocessor (not shown) for appropriate decoding of the binary information.

Figure 4:
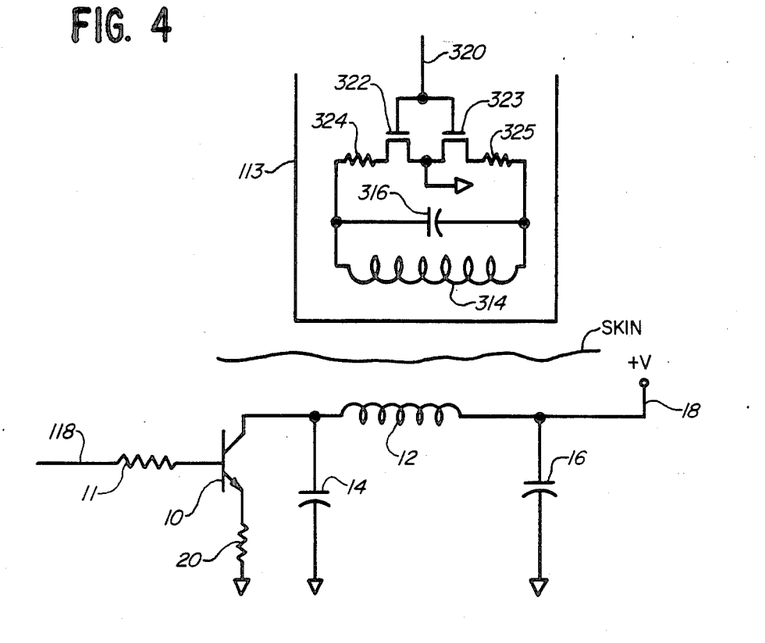
FIG. 4 is a schematic circuit diagram of the telemetry tank and the implanted tank circuit of the present invention.

Referring now to FIG. 4 of the drawings, there is shown in more detail the switching transistor 10 with the telemetry tank in the external programming and telemetry unit 1 and the implanted pacer 113. The pacer 113 includes a tank circuit comprised of a tuned coil 314 and a capacitor 316 and a shunt circuit for varying the inpedance of the tank circuit in accordance with an input data signal on line 320. The line 320 is connected to the common gate of a pair of field-effect transistors (FET) 322 and 323. The sources of the transistors 322 and 323 are connected together and to a ground potential of the implanted pacer 113. The drain of the transistor 322 is connected to one end of the tank circuit via a resistor 324, and the drain of the transistor 323 is connected to the other end of the tank circuit via a resistor 325.

The impedance of a telemetry tank consisting of the telemetry coil 12 and the capacitor 14 is matched to the impedance of the pacer 113. The impedance of the pacer includes the implanted tank circuit as well as the pacer housing itself. Further, the resistance value of the resistor 20 is matched to the complex impedance of the telemetry tank. In a preferred embodiment, it was found that the pacer has an impedance of 270 ohms. Thus, the complex impedance of the telemetry tank was made to be also 270 ohms as well as resistance value of the resistor.

Figure 5:
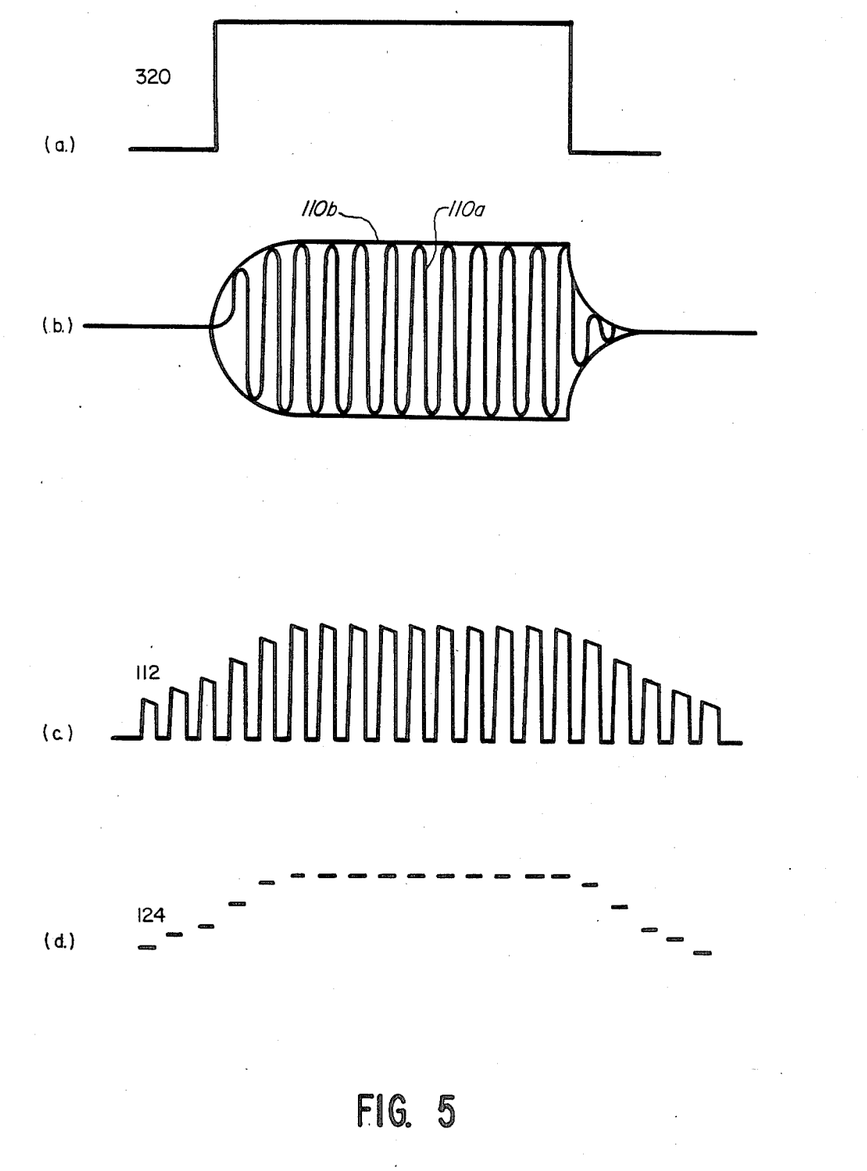
FIG. 5, lines (a)-(d) are another set of waveform diagrams useful in understanding the operation of the present invention.

While the drive current pulses on the line 108 applied to the base of the transistor 10 are all equal in size. The drive current pulses at the emitter of the transistor 10 are influenced by the data signal on the line 320 transmitted from the pacer 113 to the telemetry coil 12. As a result, there is caused a loading or unloading of the telemetry tank which changes its complex impedance. Since the resistor 20 is effectively in series with the telemetry coil 12 during the drive current pulse, there will be an increased voltage across the resistor 20 when there is a voltage drop across the telemetry coil 12. Therefore, the drive current pulses at the emitter of the switching transistor will vary in amplitude and frequency in response to the data signal applied on the line 320 and to the proximity of the external programming and telemetry unit with the respect to the implanted pacer. Thus, the signal at the emitter will represent both the proximity information and the reflected telemetry information. In FIG. 5, line (a) there is shown in an expanded form the data signal applied to the line 320 in the form of the binary pulse-width modulated signal. The output signal at the collector of the transistor 10 on the line 110 is illustrated in FIG. 5, line (b) which is a sinusoidal waveform (sinewave) 110a enclosed by an envelope 110b. The drive current pulses generted at the emitter of the transistor 10 are depicted in FIG. 5, line (c) which are varied in amplitude and frequency. Thus, the sampled drive current pulses forming the sample and hold signal at the output of the second sample and hold circuit on the line 124 is shown in FIG. 5, line (d). It will be noted that these sampled values of the drive pulses on the line 124 follow the general shape of the envelope 110b in FIG. 5, line (b). From these sampled values, the telemetered data signals that are generated by the implanted tank circuit are reconstructed.

Figure 6A:
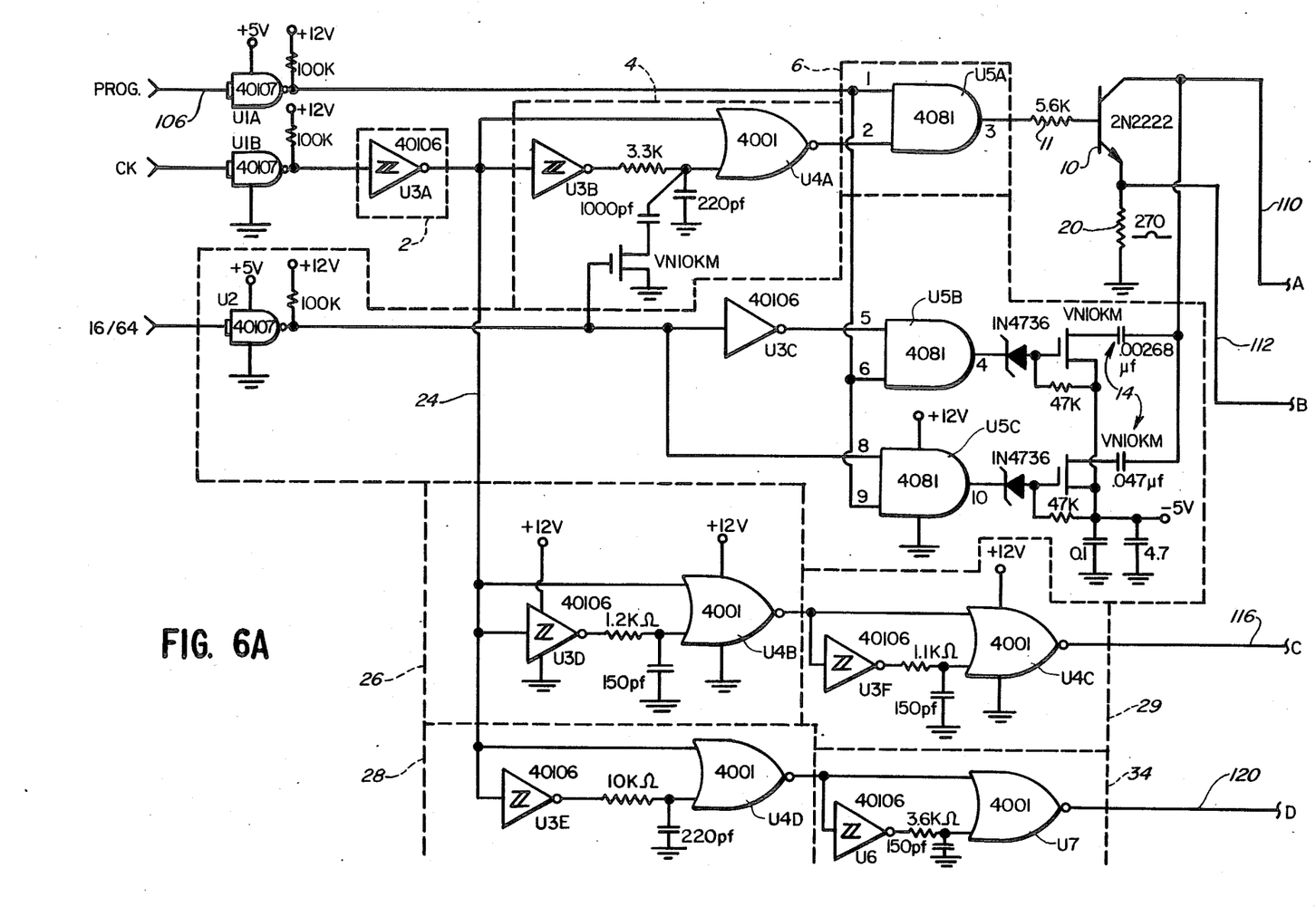
FIGS. 6A and 6B, when connected together, form a schematic circuit diagram showing circuitry suitable for use in certain of the blocks depicted in FIG. 1.
Figure 6B:
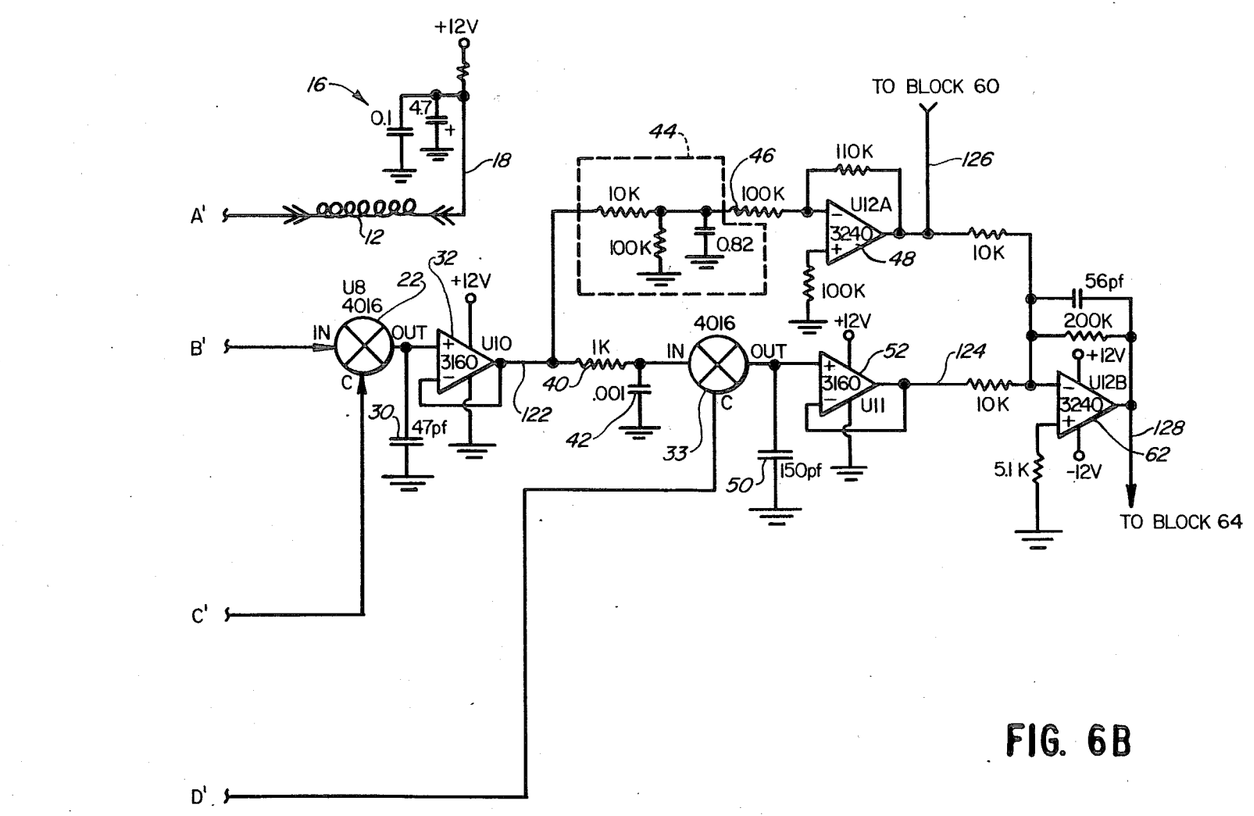

While the various blocks in FIG. 1 may take various forms, suitable circuitry for use in certain blocks thereof are illustrated in FIG. 6 A and FIG. 6 B. Since these electronic circuits are quite conventional in nature, it is believed that the schematic diagrams are self-explanatory to those skilled in the art and thus a detailed description of the operations of each circuit is believed to be unnecessary.

For completeness in the disclosure of the above described telemetry system but not for purpose of limitations, the representative values and component identifications have been included in the schematics of FIG. 6A and FIG. 6B. These values and components were employed in a telemetry system that was constructed and tested and which provided a high quality performance. It should be readily apparent to those skilled in the arts that many alternatives elements and values may be employed in constructing the various circuits in accordance with the present invention.

Figures 7, 8, 9, 10:
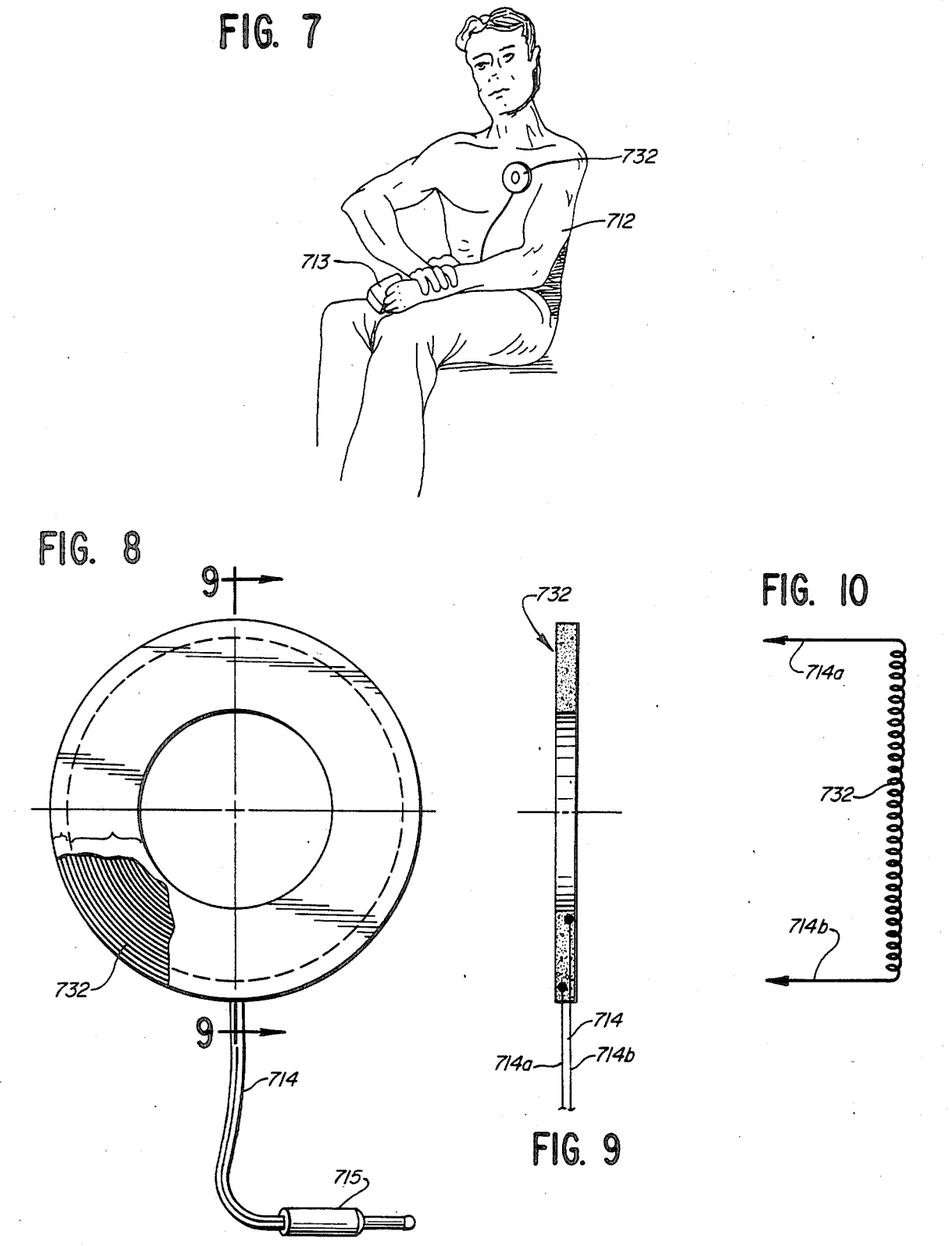
FIG. 7 illustrates a patient using the telemetry system of the present invention.
FIG. 8 is a plan, elevational view, partly broken, of an inductor coil used in connection with the present invention.
FIG. 9 is a cross-sectional view of the inductor coil, taken along the lines 9—9 of FIG. 8.
FIG. 10 is a schematic representation of the winding for the inductor coil of FIGS. 8 and 9.

In FIG. 7, there is shown a patient 712 using the external programming and telemetry unit of the present invention which is comprised of a housing 713 and a separated inductor coil or patient's coil 732. The inductor coil 732 corresponds to the telemetry coil 12 in the FIGS. 1 and 4. The inductor coil 732 is affixed to the patient's skin and is coupled to the housing 713 via a flexible electrical cord 714 and an electrical plug 715 (FIG. 8). The housing 713 contains all of the external programming and telemetry circuits of the unit 1 in FIG. 1, except for the telemetry coil 12 which is separated from the housing. The coil 732 comprises 150 turn of No. 28 copper wire having a central circular opening with a diameter approximately $1\frac{3}{4}$ inches and outer diameter of approximately of $2\frac{3}{8}$ inches. The coil has a generally disc-shape configuration with a thickness of approximately 0.100 inches, as can best be seen from FIG. 9.

Referring to FIGS. 9 and 10, the ends 714 (a) and 714 (b) of the winding 732 form the flexible electrical cord 714. It is preferrable that the winding have a thermoplastic coating so that they may be heated to form an integral unit. The coil or winding 732 is wound on a bobbin, pulled off, and then encapsolated with an appropriate potting compound such as a thermosettng potting material. The coil 732 which is positionable externally on the patient's skin in proximity to or substantially overlying the implanted tank circuit is extremely light weight and small. Further, it can be manufactured with relative ease and economy, may be made sterilizable, and may be reuseable. In a preferrred embodiment, both faces of the patient's coil 732 are flat so that it may be placed against the patient's skin and may be readily attached to the skin allowing the patient to wear it for a relatively long period of time. Since a spherical electromagnetic field lobe is produced with a diameter of approximately 6 inches with the above coil demension, this affords a significant amount of latitude with respect to obtaining signals even if the patient's coil 732 is not placed exactly over the implanted pacer.

From the foregoing detailed description, it can thus be seen that the present invention provides an improved telemetry system for cummunicating with an implanted cardiac pacer which samples each drive current pulse applied to a telemetry tank for recovering telemetered data from the pacer. Further, the telemetry system of the instant invention permits the recovery of data from the implanted pacer at data rates in excess of 4k baud and yet is free of any carrier noise in the data recovered.

While there has been illustrated and described what is at present to be considered a preferred embodiment of the present invention, it will be understood by those skilled in the art that various changes and modifications may be made, and equivalent may be substituted for elements thereof without departing from the true scope of the invention. In addition, many modifications made be made to adapt a particular situation or material to the teachings of the invention without departing from the central scop thereof. Therefore, it is intended that this invention not be limited to the particular embodiment disclosed as the best mode contemplated for carrying out this invention, but that the invention will include all embodiments falling within the scope of the appended claims.

What is claimed is:

1. A telemetry system for communicating with a tank circuit contained in a pacer implanted in a patient comprising:
   telemetry coil being positionable externally on the patient's skin in proximity to the implanted pacer;
   capacitive means connected to said telemetry coil for forming a resonant tank;
   said resonant tank having a varying impedance in response to telemetered data signals from the implanted tank circuit;
   clocking means for generating drive current pulses at a selected frequency to be applied to said resonant tank;
   switching means for generating a pulse waveform having a varying amplitude and frequency in response to the drive current pulses and to the varying impedance of said resonant tank;
   means sampling the pulse waveform of varying amplitude and frequency to provide a sample and hold signal; and
   output means coupled to said sampling means for recovering of the telemetered data signals in the form of a binary pulse-width modulated signal.

2. A telemetry system as claimed in claim 1, wherein said clocking means for generating said drive current pulses includes a clock oscillator having a frequency of 16 kilohertz.

3. A telemetry system as claimed in claim 1, wherein said clocking means for generating said drive current pulses includes a clock oscillator have a frequency of 64 kilohertz.

4. A telemetry system as claimed in claim 1, wherein said clocking means for generating said drive current pulses includes an oscillator frequency selector for tuning said resonant tank at either 16 kilohertz or 64 kilohertz.

5. A telemetry system as claimed in claim 1, wherein said switching means includes a transistor having its collector connected to said resonant tank and its emitter connected to a resistor, the output of the resistor providing said pulse waveform.

6. A telemetry system as claim in claim 1, wherein said sampling means includes a pair of sample and hold circuits connected in series to function as a clocked filter.

7. A telemetry system as claimed in claim 1, further comprising an offset tracking filter being responsive to said sample and hold signal to provide a DC signal level representative of the distance of the telemetry coil to the implanted pacer.

8. A telemetry system as claimed in claim 7, wherein said output means comprises amplifier means for summing said DC signal level and said sample and hold signal to generate the pulse-width modulated signal.

9. A telemetry system as claimed in claim 7, further comprising acquisition circuit means responsive to said DC signal level for providing a visual indication which increases in intensity when the telemetry coil is closer in proximity to the implanted pacer.

10. A telemetry system as claimed in claim 1, further comprising program logic means responsive to a program signal for transmitting drive current pulses to the implanted tank circuit so as to program said implanted pacer.

11. In a telemetry system for pacing in which a pacer containing a data modulated tank circuit is implanted in a patient and a program and telemetry unit is used external of the patient, the improvement comprising in combination:
    telemetry coil being positionable externally on the patient's skin in proximity to the implanted pacer;
    capacitive means connected to said telemetry coil for forming a resonant tank;
    said resonant tank having a varying impedance in response to telemetered data signals from the implanted tank circuit;
    clocking means for generating drive current pulses at a selected frequency to be applied to said resonant tank;
    switching means for generating a pulse waveform having a varying amplitude and frequency in response to the drive current pulses and to the varying impedance of said resonant tank;
    means sampling the pulse waveform of varying amplitude and frequency to provide a sample and hold signal; and
    output means coupled to said sampling means for recovering of the telemetered data signals in the form of a binary pulse-width modulated signal.

12. A telemetry system as claimed in claim 11, wherein said clocking means for generting said drive current pulses includes a clock oscillator have a frequency of 64 kilohertz.

13. A telemetry system as claimed in claim 11, wherein said clocking means for generating said drive current pulses includes an oscillator frequency selector for tuning said resonant tank at either 16 kilohertz or 64 kilohertz.

14. A telemetry system as claimed in claim 11, wherein said switching means includes a transistor having its collector connected to said resonant tank and its emitter connected to a resistor, the output of the resistor providing said pulse waveform.

15. A telemetry system as claim in claim 11, wherein said sampling means includes a pair of sample and hold circuits connected in series to function as a clocked filter.

16. A telemetry system as claimed in claim 11, further comprising an offset tracking filter being responsive to said sample and hold signal to provide a DC signal level representative of the distance of the telemetry coil to the implanted pacer.

17. A telemetry system as claimed in claim 16, wherein said output means comprises amplifier means for summing said DC signal level and said sample and hold signal to generate the pulse-width modulated signal.

18. A telemetry system as claimed in claim 16, further comprising acquisition circuit means responsive to said DC signal level for providing a visual indication which increases in intensity when the telemetry coil is closer in proximity to the implanted pacer.

19. A system for detecting proximity of an external program and telemetry unit with respect to an implanted pacer comprising:
- telemetry coil being positionable externally on the patient's skin substantially overlying the implanted pacer;
- capacitive means connected to said telemetry coil for forming a resonant tank;
- said resonant tank having a varying impedance in response to telemetered data signals from the implanted tank circuit;
- clocking means for generating drive current pulses at a selected frequency to be applied to said resonant tank;
- switching means for generating a pulse waveform having a varying amplitude and frequency in response to the drive current pulses and to the varying impedance of said resonant tank;
- means sampling the pulse waveform of varying amplitude and frequency to provide a sample and hold signal; and
- an offset tracking filter being responsive to said sample and hold signal to provide a DC signal level representative of the distance of the telemetry coil to the implanted pacer.

20. A system for detecting proximity as claimed in claim 19, further comprising acquisition circuit means responsive to said DC signal level for providing a visual indication which increases in intensity when the telemetry coil is closer in proximity to the implanted pacer.

* * * * *